(12) United States Patent
Cabeza Guillen et al.

(10) Patent No.: US 8,827,451 B2
(45) Date of Patent: Sep. 9, 2014

(54) EYESIGHT TESTING DEVICE

(71) Applicant: Carl Zeiss Vision International GmbH, Aalen (DE)

(72) Inventors: Jesus-Miguel Cabeza Guillen, Aalen (DE); Michael Gamperling, Leipheim (DE); Matthias Kubitza, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 13/724,961

(22) Filed: Dec. 21, 2012

(65) Prior Publication Data

US 2013/0188127 A1    Jul. 25, 2013

(30) Foreign Application Priority Data

Dec. 22, 2011   (DE) .......................... 10 2011 089 705

(51) Int. Cl.
*A61B 3/08*    (2006.01)
*A61B 3/00*    (2006.01)

(52) U.S. Cl.
USPC ............................ 351/202; 351/201; 351/246

(58) Field of Classification Search
USPC ................................................ 351/200–246
See application file for complete search history.

(56) References Cited

U.S. PATENT DOCUMENTS

| | | | | |
|---|---|---|---|---|
| 5,331,358 | A | * | 7/1994 | Schurle et al. ................ 351/232 |
| 5,877,840 | A | | 3/1999 | Yamada et al. |
| 5,943,166 | A | * | 8/1999 | Hoshi et al. .................... 359/475 |
| 6,350,032 | B1 | * | 2/2002 | Menozzi et al. ............... 351/239 |
| 6,726,327 | B2 | * | 4/2004 | Torrey et al. .................. 351/243 |
| 2010/0060983 | A1 | | 3/2010 | Wu et al. |
| 2012/0182407 | A1 | | 7/2012 | Yoshida |

OTHER PUBLICATIONS

English translation and Office action of the German Patent Office dated Sep. 21, 2012 in German patent application 10 2011 089 705.4 on which the claim of priority is based.

* cited by examiner

*Primary Examiner* — Mohammed Hasan
(74) *Attorney, Agent, or Firm* — Walter Ottesen P.A.

(57) ABSTRACT

An eyesight testing apparatus examines associated heterophoria of the eyes of a subject. The apparatus includes an image generation device having a display unit for generating test patterns for display to the eyes. An optical assembly is arranged on that side of the display unit facing the eyes. This assembly separates light supplied by a first group of selected zones of the display unit from light supplied to a beam path by a second group of selected zones of the display unit. The left eye only receives the light from the first group. The light from the second group only passes to the right eye. The optical assembly includes a prism matrix having a multiplicity of prism portions extending in the vertical direction and each having a lens-shaped region with a convex surface facing the display unit.

21 Claims, 9 Drawing Sheets

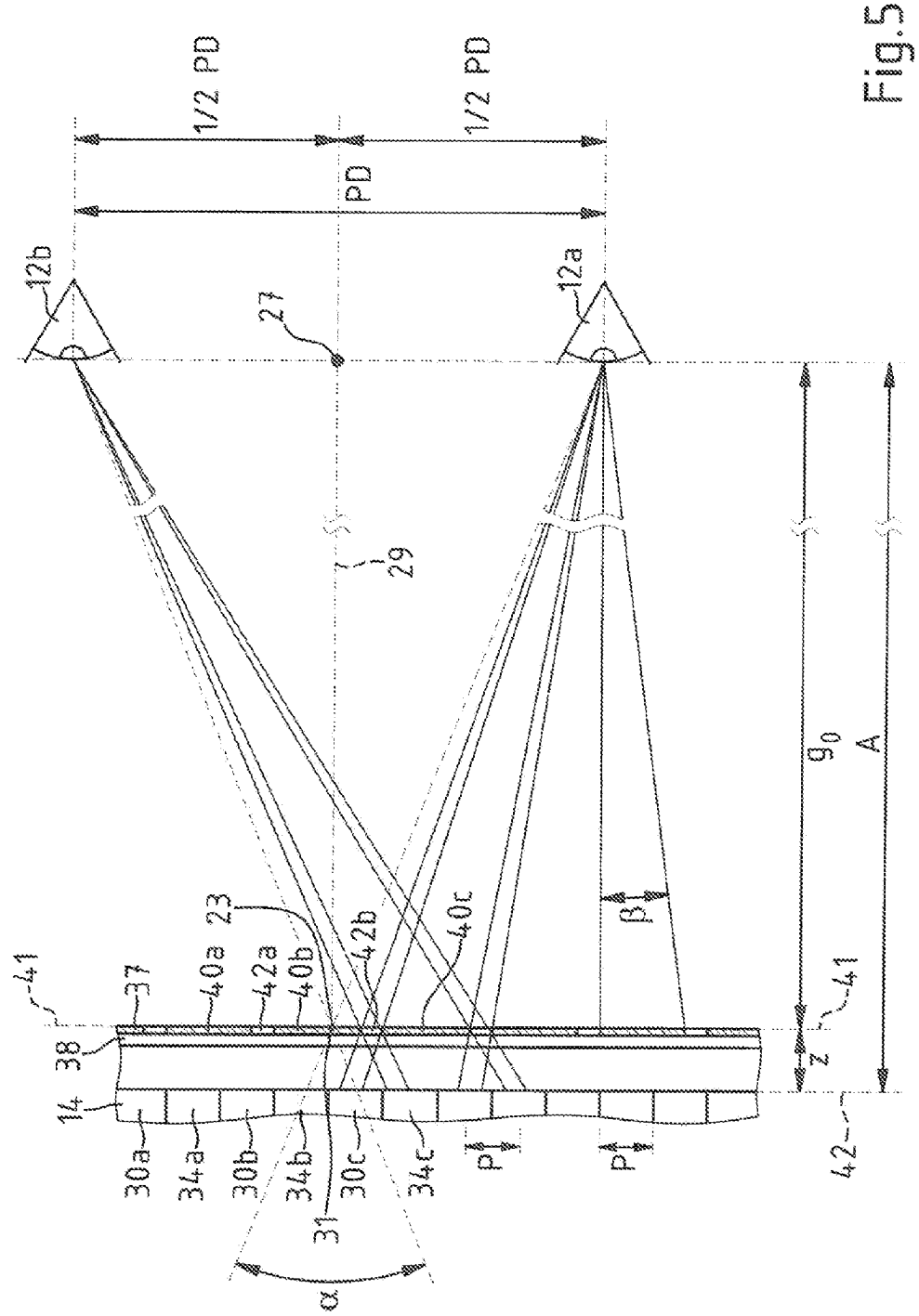

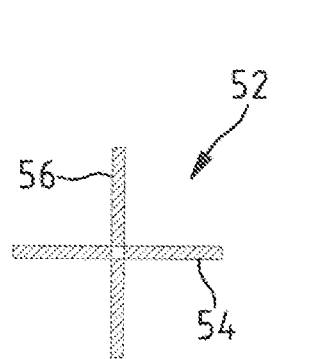
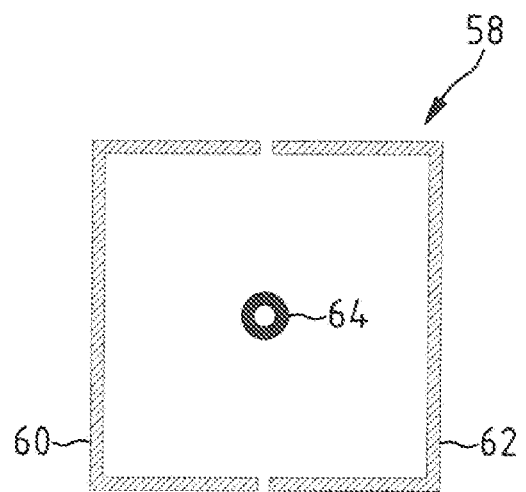
Fig.7a　　　　　　　　Fig.7b
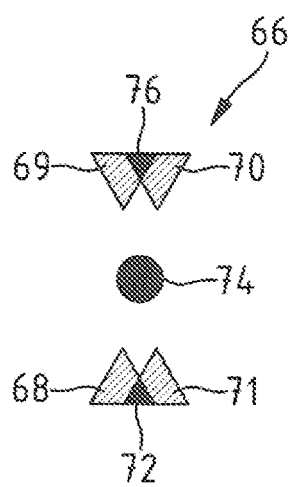
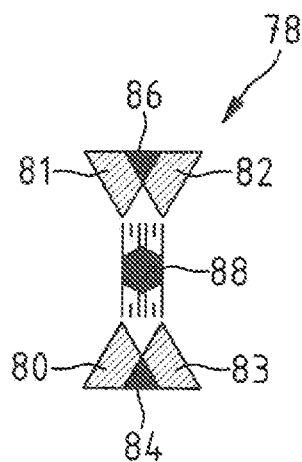
Fig.7c　　　　　　　　Fig.7d

EYESIGHT TESTING DEVICE

CROSS REFERENCE TO RELATED APPLICATION

This application claims priority of German patent application no. 10 201.1 089 705.4, filed Dec. 22, 2011, the entire content of which is incorporated herein by reference.

FIELD OF THE INVENTION

The invention relates to an eyesight testing device for examining associated heterophoria of the eyes of a subject, having an image generation apparatus containing a display unit for producing test patterns, which can be displayed to the eyes of the subject with an optical beam path.

BACKGROUND OF THE INVENTION

Eyesight testing devices for examining associated heterophoria of the eyes of a subject are known (for example, U.S. Pat. No. 5,331,358). The eyesight testing device described therein contains a first LCD display unit and a second LCD display unit. The first LCD display unit and the second LCD display unit are arranged one behind the other. The eyesight testing device contains a light source, which illuminates the LCD display units with transmitted light. On the light incidence side of one of each of the two display units, in each case a colour-neutral, see-through polarizer is arranged. The polarizers have polarization axes, which differ with respect to one another. In order to examine the eyes of a subject using the eyesight testing device, the subject wears polarized glasses, which have lenses with polarization directions which are different for the right and left eyes and in each case correspond, to the polarization axes of the polarizers. The displays on the first and second LCD display units are thus separated owing to the different polarization of light. As a result, if the subject's head is tilted to the side, the information displayed on the two LCD display units is no longer visualized in a clearly separated manner.

SUMMARY OF THE INVENTION

It is the object of the invention to provide an eyesight testing device, with which associated heterophoria of the eyes of a subject can be examined and the dependence of the visual impression of the subject on the head position is reduced.

In an eyesight testing device according to the invention, on that side of the display unit facing the eyes of the subject in the optical beam path, an optical assembly is arranged, which separates the light supplied by a first group of selected zones of the display unit to the optical beam path from the light which is supplied to the beam, path by a second group of selected zones of the display unit in order to supply the light from the first group of selected zones of the display unit to the left eye of the subject and to guide the light from the second group of selected zones of the display unit to the right eye of the subject. The display unit in the eyesight testing device can be, for example, an LCD display unit, an LED display unit or an OLED display unit.

One idea of the invention is to provide an optical assembly with a prism matrix in the eyesight testing device. By the prism matrix having a multiplicity of prism portions, which extend in the vertical direction and each have a lens-shaped, in particular cylindrical-lens-shaped region with a convex surface facing the display unit, various test patterns with a beam path which is directed onto a preferred position of the subject can be visualised to a subject during an eyesight test. This has the advantage that the presence or absence of a visual defect can be concluded with a great degree of reliability from the visual impression of a pattern that is visualized to a subject during an eyesight test. Moreover, it is possible with such a prism matrix for partial images, which are separated exactly from one another, to be displayed to a subject even when the head position or the distance front the eyesight testing device in the left and right eyes changes.

The eyesight testing device can be used, for example, in an examination system having a subject region, in which, for performing an eyesight test, a subject can be positioned at a distance A from the display unit of the eyesight testing device, for which: 1 m≤A≤7 m, preferably 2 m≤A≤3 m. A seating device arranged in the subject region is preferably provided in the examination device.

In an alternative embodiment of the invention, the optical assembly can, however, also contain a screen system acting as a parallax barrier for separating the light of the first and second groups of selected zones of the display unit. To this end, the screen system can be configured, for example, as a mask with alternately light-transmissive and opaque regions.

For defining the course of the optical beam path to the eyes of the subject, it is advantageous if the optical assembly is adjustable. This makes it possible for the visual impression that can be created in the subject with the eyesight testing device to be matched to the position of the subject.

The horizontal width $B_{Mn}$ of the opaque regions of the mask in the screen system is preferably at least twice the width $B_{Md}$ of the light-transmissive regions of the mask. What is achieved with this measure is that the information displayed to the left and the right eyes of the subject with the display unit for the subject is separated exactly for the left and right eyes not only in cases where the head position is inclined forwards or backwards, but also when the head of a subject is tilted to the side. With respect to the separation of the image information for the left and right eyes of a subject, the eyesight testing system according to the invention is thus far less sensitive to the subject's head position than conventional eyesight testing devices, which are based on the principle of separating this image information using polarised light.

By the screen system being moveable perpendicular and/or parallel relative to the display unit, in particular by the distance z between the light passage plane, separating the light for the left and right eyes, of the screen system and the display unit being able to be varied, the eyesight testing device can be adjusted for various distances and head positions of the subject.

It is advantageous in particular if the eyesight testing device contains a device for capturing the angular position of the eyes of a subject with respect to the mask and is connected to a drive, with which the screen system can be shifted, on the basis of a captured angular position, of the eyes of the subject, preferably parallel to the plane of the display unit, alternatively or additionally also perpendicularly to the plane of the display unit, such that the deviation S of the center of the perpendicular projection of the pupillary distance of the eyes of the subject from a vertical line through the geometric center of the mask before the shift and a vertical, displacement V of the geometric center of the mask after the shift satisfies the following relationship:

$$\frac{V}{z} = \frac{S}{g}.$$

Here, z is the distance of the light passage plane of the screen system from the display unit and g is the distance of the subject from the light passage plane of the screen system. Such an eyesight testing device can be configured in particular for automatically tracking the mask in order to display to a subject test patterns which are separated for the left and right eyes, even if the subject changes his head position.

Suitable for moving the screen system relative to the display unit is, for example, a motorized, in particular an electromotive, a piezoelectric, a magnetostrictive or a micromechanical drive.

It is expedient if the display unit has a multiplicity of pixels far producing image points in adjoining, mutually complementary stripe-shaped display-unit zones, which preferably extend in the vertical direction. Mutually complementary display-unit zones are here understood to mean display-unit zones which make possible the simultaneous production of different partial images on a display unit.

The alternately light-transmissive and opaque regions of the mask can have a stripe shape and be arranged parallel to the display-unit zones.

It is advantageous if the width $B_{Mu}$ of the regions of the mask which are opaque for light from the display unit and the width $B_{Md}$ of the regions of the mask which are transmissive for light from the display unit and the width $B_D$ of the stripe-shaped display-unit zones satisfy the following relationship:

$$B_{Mu} \sim 3 \, B_{Md} \sim 3/2 B_D.$$

wherein the distance z of the mask from the display unit corresponds to 25 to 50 times the width $B_D$ of the display-unit zones.

It is advantageous in particular if the width $B_D$ of the stripe-shaped display-unit zones and/or the width $B_M$ of the stripes of the stripe mask can be adjusted. It is thus possible for the eyesight testing device to be matched to the pupillary distance of the eyes of a subject and to the head position of the subject. The width $B_D$ of the stripe-shaped display-unit zones preferably corresponds to the diameter P of a display unit pixel for the generation of an image point.

One idea of the invention is furthermore to use the eyesight testing device and/or the examination device for carrying out the cross test or the pointer test or the rectangle test or the triangle test or the stereo balance test. Moreover, the invention also extends to the testing of visual functions of the eyes of a subject with an eyesight testing device or with an examination device, in which the first and the second groups of selected regions of the display unit are used to produce two partial patterns, which are mutually complementary at least, in portions, in particular for performing the cross test or the rectangle test or the triangle test or the stereo balance test, and in the process one of the two partial patterns is displayed to the left eye and the other partial pattern is displayed to the right eye of the subject.

BRIEF DESCRIPTION OF THE DRAWINGS

The invention will now foe described with reference to the drawings wherein;

FIG. 5 shows a section through the eyesight testing device along the line IV-IV in FIG. 1;

FIGS. 7a to 7d show different test patterns which can be displayed in the examination device to a subject;

DESCRIPTION OF THE PREFERRED EMBODIMENTS OF THE INVENTION

Figure 1:
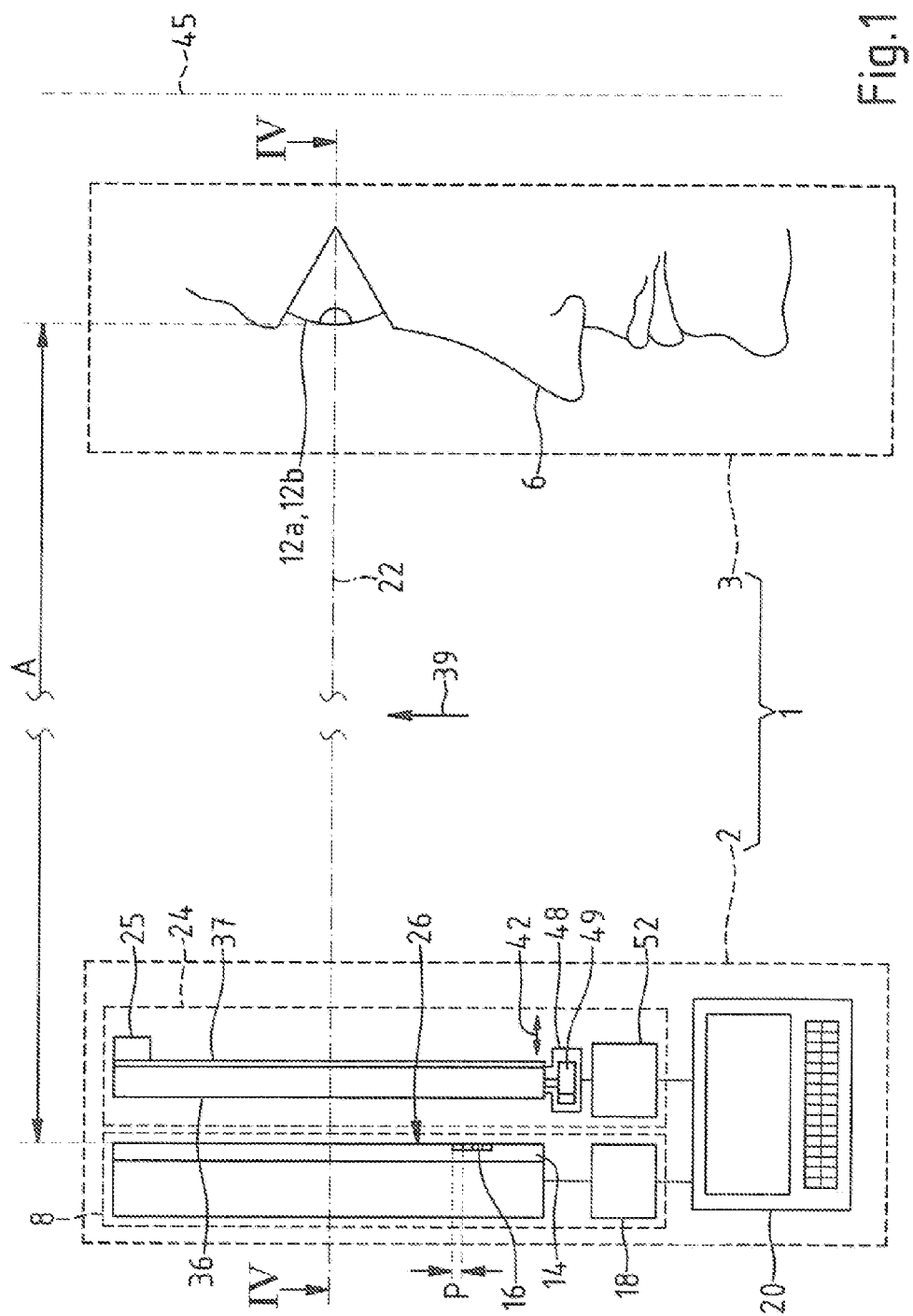
FIG. 1 snows a first examination device with an eyesight testing device.

The examination device 1 shown in FIG. 1 comprises an eyesight testing device 2 and has a subject region 3. The eyesight testing device 2 is configured to display to the eyes 4 of a subject 6 in the subject region 3 test patterns, which are generated using an image generation apparatus 8. A seat device (not illustrated) is situated in the subject region 3 of the examination device 1. This seat device permits the subject 6 to observe in a relaxed state test patterns produced with the image generation apparatus 8. The subject region 3 is arranged, to be at a distance from the eyesight testing device 2 such that the eyes (12a, 12b) of the subject 6 in the subject region 3 have, for example, the distance A~2.5 m from the image generation apparatus 8. In such an examination device, however, a distance A of the eyes of the subject from the image generation apparatus 8 can in principle also be provided in the region of 1 m≤A≤7 m or above.

The image generation apparatus 8 contains a display unit 14. The display unit 14 is configured as an LED matrix. For producing test patterns, the display unit 14 has a multiplicity of pixels 16, which can be driven via a driver assembly 18 with a computer unit 20. The light emitted by the pixels 16 with appropriate driving of the display unit 14 is supplied to the eyes (12a, 12b) of the subject 6 with an optical beam path 22, In an alternative embodiment of the examination system 1, it is also possible for the display of the display unit 14 to be supplied to the subject 6 with an optical beam path which is guided via one or more mirrors.

It is possible by way of the eyesight testing device 2 for a test pattern to be visualized to the eyes (12a, 12b) of the subject 6, which test pattern is composed of a test pattern supplied to the left eye 12a and a test pattern that is supplied to the right eye 12b. The partial pattern for the left eye 12a can here be displayed, with the eyesight testing device 2, to the subject 6 independently of the partial pattern for the right eye 12b.

For the independent visualization of test patterns, an optical assembly 24 is provided in the eyesight testing device 2. The optical assembly 24 contains a screen system 36 in order to separate the light from the display unit 14 for the left and right eyes (12a, 12b) of the subject. The screen system 36 comprises a mask 37, which has stripe-shaped regions which extend in the vertical direction indicated with the arrow 39 and are alternately transmissive and opaque for the light from the display unit. The optical assembly 24 separates the light, which is supplied from a first group of selected regions of the display unit 14 to the optical beam path 22, from the light the beam path 22 receives from a second group of selected regions of the display unit 14. A camera 25 is provided in the eyesight testing device 2. The camera 25 is connected to the computer 20.

Figure 2:
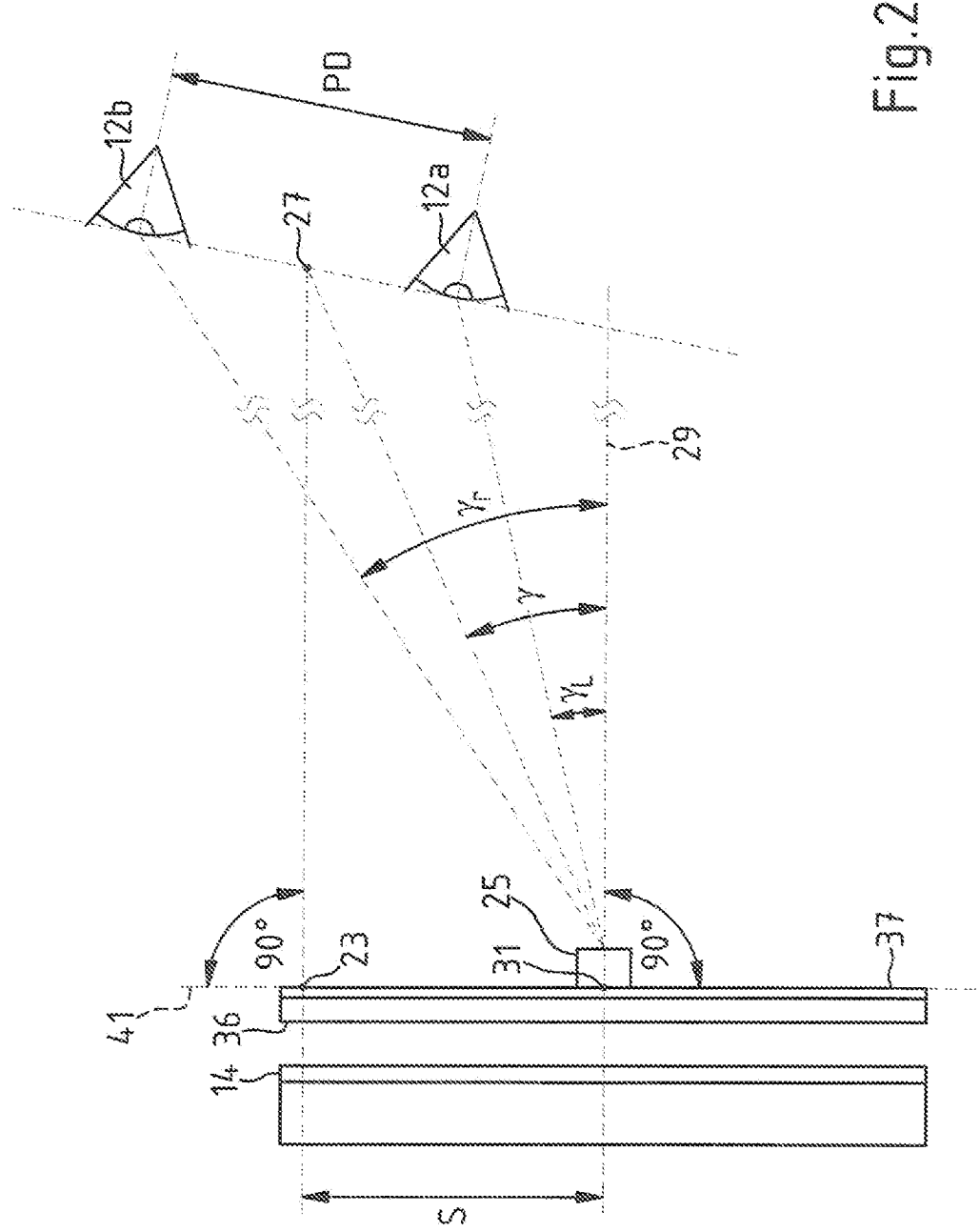
FIG. 2 shows the capturing of the angular position of the eyes of a subject with a camera in the eyesight testing device.

FIG. 2 shows a portion of the eyesight testing device 2 in a view from above. Using the camera 25, the angular position of the eyes (12a, 12b) of the subject 6 with respect to the mask 37 can be captured. The computer 20 in the eyesight testing device 2 to this end contains an image evaluation program. This can be used to determine, on the basis of an image of the subject captured with the camera 25, the angle $$\gamma := \frac{1}{2}\{\gamma_l + \gamma_r\}$$

of the center 27 of the pupillary distance PD of the subject with respect to the surface normal 29 on the vertical line 31 through the geometric center, that is, the middle of the mask 37. The computer 20 to this end uses the program to first ascertain the center of the pupils (31a, 31b) of the eyes (12a, 12b) of the subject. Therefrom the computer determines the angle γ, with which the camera 25 captures the center 27 of the pupillary distance PD with respect to the surface normal 29 through the geometric center of the mask 37.

Figure 3:
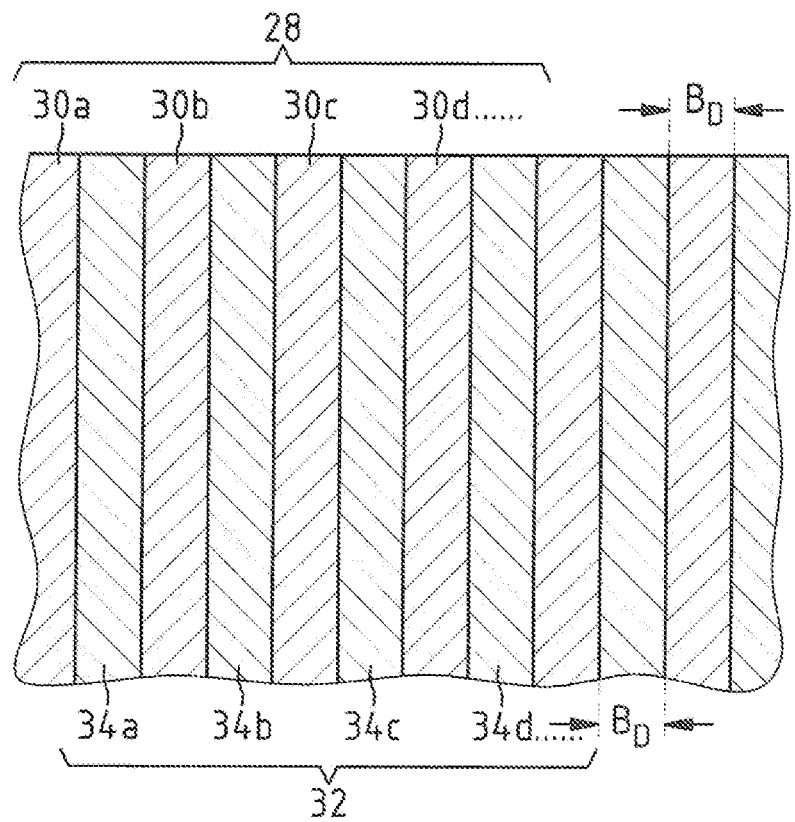
FIG. 3 shows a plan view of the optically active side of a display unit in the eyesight testing device.

FIG. 3 shows a portion of the optically active side 26 of the display unit 14 in the eyesight testing device 2. The display unit 14 has a first group 28 of stripe-shaped display-unit zones 30a, 30b, 30c, 30d . . . and has a second group 32 of stripe-shaped display-unit zones 34a, 34b, 34c, 34d. . .

The display-unit zones 34a, 34b, 34c, 34d, . . . are complementary to the display-unit zones 30a, 30b, 30c, 30d, . . . That is to say the surface of at least; one of the display-unit zones 34a, 34b, 34c, 34d and the surface of at least one of the display-unit zones 30a, 30b, 30c, 30d, . . . touch each other and cover the display unit 14 in at least one portion in a contiguous manner.

The display-unit zones (30, 34) can be selected using the computer unit 20 of the eyesight testing device shown in FIG. 1. The computer unit 20 is used to produce in the display-unit zones 30a, 30b, 30c, . . . a partial pattern for the left eye 12a of the subject 6. Accordingly, the display-unit zones 32 are used to generate a partial pattern for the right eye 12b of the subject. The partial pattern produced in the display-unit group 28 is in this case complementary to the partial pattern displayed in the display-unit zones 32. The display-unit zones 30a, 30b . . . and 34a, 34b, 34c have a constant width $B_D$. The width $B_D$ corresponds to the diameter P of a pixel 16 on the display unit 14, that is, to the minimum diameter of an image point in an image, which can be displayed using the display unit 14.

Figure 4:
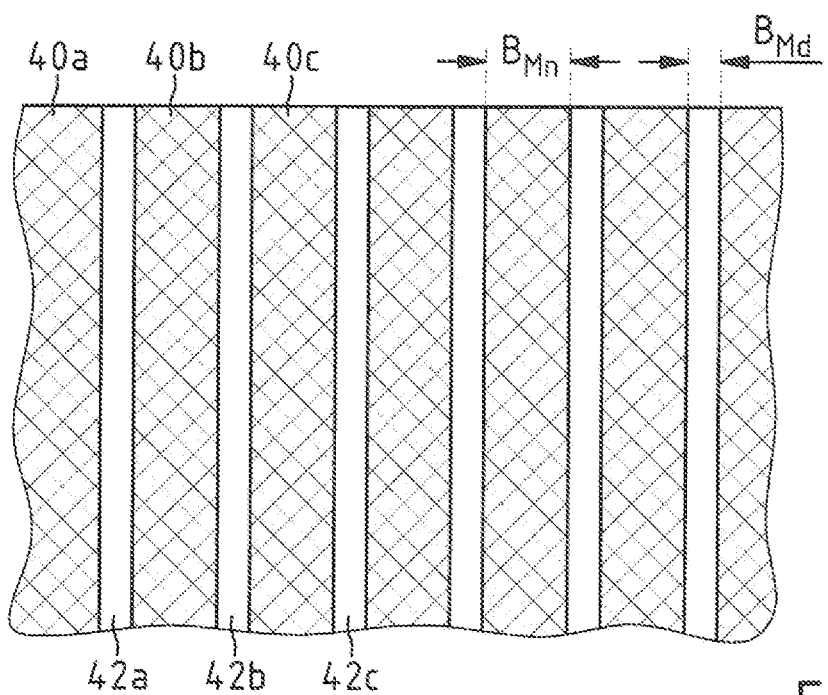
FIG. 4 shows a plan view of a screen system in the eyesight testing device.

FIG. 4 shows a portion of the mask 37 in a plan view. The mask 37 is a stripe mask. The mask 37 acts as a parallax barrier. The stripe-shaped regions 40a, 40b, 40c, . . . of the mask 37 are opaque for the light from the display unit 14. The other way around, the regions 42a, 42b, 42c, . . . of the mask 37 of the screen system 36 are transmissive for the light from the display unit 14. The width $B_{Md}$ of the regions 42a, 42b, 42c, . . . which are transmissive for the light from the display unit 14 is $B_{Md}=1/2\,8_D$. The width $B_{Mn}$ of the regions 40a, 40b, 40c, . . . of the mask 37 which are opaque for light is one and a half times as large as the width $B_D$ of the display-unit zones 30a, 30b, 30c, . . . , that is, $B_{Mn}=3/2\,B_D$. The mask 37 thus has a translation invariance. By shifting the structure of the mask 37 in the horizontal direction by the distance $$S := B_{Md} + B_{Mn}$$

the structure is transformed into itself.

FIG. 5 is a partial section through the eyesight testing device along the line IV-IV in FIG. 1. The mask 37 of the screen system 36 is arranged on a see-through carrier element 38. By way of the stripe-shaped regions (40a, 40b, 40c; 42a, 42b, 42c), which are transmissive and opaque for the light from the display unit 14, the mask 37 separates the light for the left and right eyes (12a, 12b) of the subject 6 in the light passage plane 41.

The light passage plane 41 of the mask 37 is freely shiftable in the eyesight testing device 2. To this end, the eyesight testing device 2 contains, as shown in FIG. 1, a moving device 48 for the screen system 35. The moving device 48 can be used to move the screen system 36 in the horizontal direction in accordance with the double-headed arrow 42 shown in FIG. 1 and in the horizontal direction perpendicular to the direction of the double-headed arrow 42. For the purposes of moving, the moving device 48 contains a piezoelectric drive 49, which can be controlled by the display unit 14 via a driver assembly 52 using the computer 20 in dependence on the angular position of the eyes (12a, 12b) of the subject 6 captured with the camera 25. The moving device 48 makes it possible for the distance z of the plane 42 of the display unit 14 from the light passage plane 41 of the mask 37 to vary in the range of 8 mm≤z≤15 mm. In accordance with the center 27 of the pupillary distance PD captured using the computer 20 and the camera 25, the moving device 48 is used to adjust and track the screen system 36 such that the straight line 29 through the center 27 and the vertical line 31 strikes the border between two neighboring display-unit zones behind the mask 37 in the plane of the display unit 14. The position of the display-unit zones 30a, 30b, 30c, . . . and of the display-unit zones 34a, 34b, 34c, . . . of the display unit 14 is matched here to the shift of the mask 37. For the purpose of moving the screen system 36, the computer 20 determines from the angle γ, under which the camera 25 captures the center 27 of the pupillary distance PD with respect to the surface normal 29 in the center 31 of the mask 37, a favorable horizontal displacement V of the mask 37 parallel to the arrow 39, that is, perpendicular to the longitudinal direction of the stripe-shaped regions of the mask 37 shown in FIG. 4 and parallel to the light passage plane 41, with $$V := z \tan \gamma.$$

The favorable displacement of the mask 37 thus satisfies the following relationship:

$$\frac{V}{z} = \frac{S}{g}$$

Here, S is the deviation, shown in FIG. 2, of the center 23 of the perpendicular projection of the pupillary distance PD in the plane 41 of the mask 37 from the surface normal 29 on the vertical line 29. g is the distance of the subject from the light passage plane 41 of the screen system 36.

In an embodiment of the invention which is modified with respect to the above-described embodiment, the screen system 36 can additionally also be moved in the vertical direction perpendicular to the double-headed arrow 42.

The subject 6 having the pupillary distance PD sees the display-unit zones 30a, 30b, 30c, . . . and 34a, 34b, 34c, . . . separately with the left eye 12a and the right eye 12b, if the following geometric relationship is satisfied;

$$\tan(\alpha/2) = \frac{PD}{2g_0} = \frac{P}{2z},$$

wherein α is the viewing angle, at which the subject 6 captures with the left and right eyes (12a, 12b) the mask 37 of the screen system 36 at the distance $g_0$, and P is the width of a stripe-shaped display-unit zone 30a, 30b, 30c, . . . , 34a, 34b, 34c. . . of the display unit 14.

The inventors have discovered that, with the assumption of infinitesimally narrow regions 42a, 42b, 42c, . . . , which are transmissive for the light from the display unit 14, a subject 6 can perceive the display-unit zones 30a, 30b, 30c, . . . and 34a, 34b, 34c, . . . in the distance region Δ with $$\frac{1}{2}g_0 \leq g_0 \mp \Delta \leq \frac{3}{2}g_0$$

in an exactly separated manner.

The inventors have also discovered that a subject 6, in particular at the distance $g_0$ from the mask 37, can also perceive the display-unit zones 30a, 30b, 30c, . . . and 34a, 34b, 34c, . . . in an exactly separated manner if the subject 6 turns his head to the left or to the right side by an angle φ of up to φ=±60° about the vertical axis 45 shown in FIG. 1. The inventors have also found that the subject 6 can moreover perceive the display-unit zones 30a, 30b, 30c, . . . and 34a, 34b, 34c, . . . in an exactly separated manner if he inclines his head to the side with respect to the axis 45 shown in FIG. 1 by an angle θ of up to θ=±60°.

The inventors have also found that, at a finite width $B_{Md}$ of the regions which are transmissive for the light from the display unit 14, the extent of this distance region is reduced by the factor $$k = 1 - \frac{B_{Md}}{B_{Mu}},$$

wherein $B_{Mu}$ is the width of the regions of the mask 37 which are opaque for light. That is to say, for the distance region Δ, in which the subject 6 perceives an image produced in the aforementioned display-unit zones separately, the following applies:

$$\Delta = \left(1 - \frac{B_{Md}}{B_{Mu}}\right)\Delta.$$

In the examination device 1 shown in FIG. 1, the width $B_{Mu}$ and $B_{Md}$ of the regions (40a, 40b, 40c, . . . ; 42a, 42b, 42c, . . . ) of the mask 37 which are opaque or transmissive for light in the eyesight testing device 2 and the distance of the subject region 6 from the eyesight testing device 2 are configured such that the viewing angle β, under which a subject 6 at the distance A from the display unit 14 with 1 m≤A≤5 m captures a region 40a, is smaller than an arcminute, i.e. β≤1. With this measure it is ensured that si typical subject eye can no longer resolve the stripe structure of the mask 37.

For a diameter P=0.3 mm of a pixel 16 of the display unit 14 and for the width $B_{Md}$=1/2 P and $B_{Mu}$=3/2 P of the step-type regions of the mask 37 which are transmissive or opaque for light, and a pupillary distance PD of the eyes (12a, 12b) of the subject 6 in the region of 60 mm≤PD≤70 mm, the partial patterns produced using the display unit 14 in the display-unit zones (30a, 30b, 30c, . . . ; 34a, 34b, 34c, . . . ) can thus be displayed in a separated manner for a distances region 2 m≤$g_0$∓Δ<3 m of the eyes (12a, 12b) of the subject 6 from the light passage plane 41 of the mask 37. The subject 6 then perceives the partial patterns produced in the display-unit zones 30a, 30b, 30c, . . . and 34a, 34b, 34c, . . . as mutually complementary partial patterns.

Figure 6A:
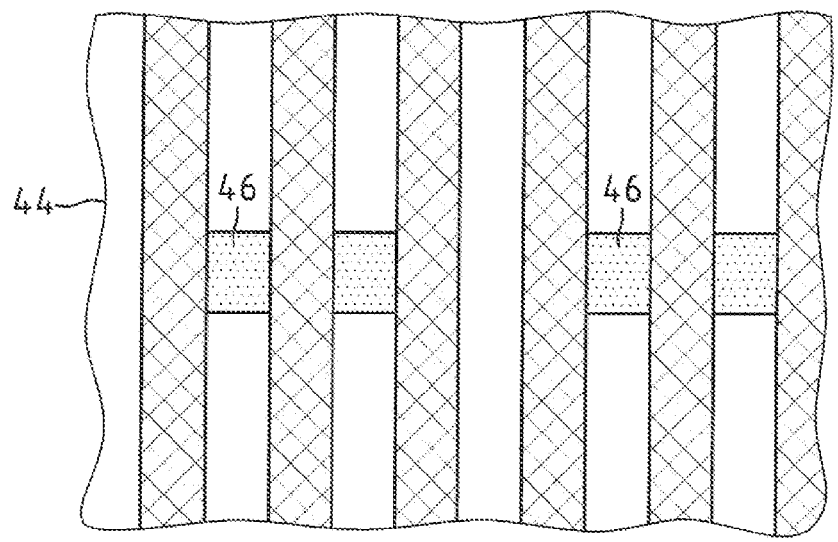
FIG. 6a shows a display of a partial pattern on the display unit for a subject's right eye.
Figure 6B:
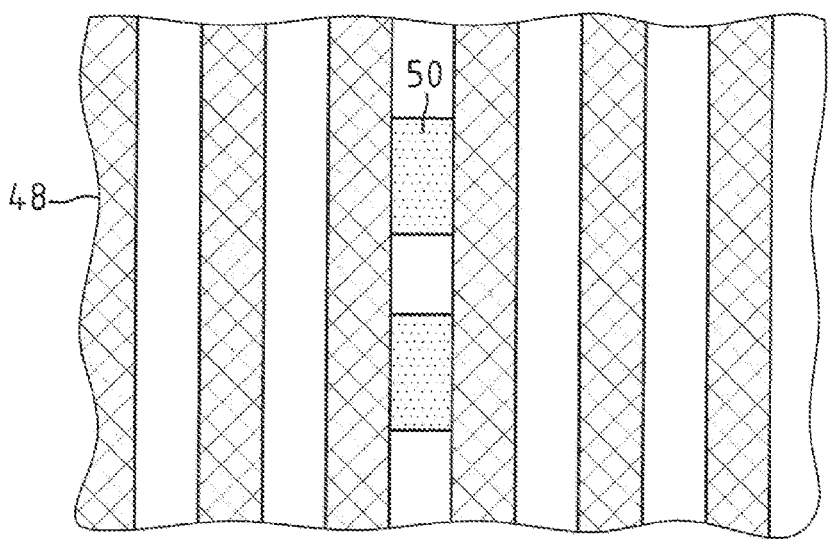
FIG. 6b shows a display of a partial pattern on the display unit for a subject's left eye.

FIG. 6a shows a portion 44 of the display unit 14 with a bar-shaped partial pattern 46 which is produced for the right eye 12b of the subject 6. FIG. 6b illustrates a bar-shaped partial pattern 50 for display for the left eye 12a of the subject 6 using the display unit 14.

FIG. 7a shows the test pattern 52 perceived by a subject when the partial patterns (54, 56) are displayed using the display unit 14. The test pattern 52 can be used to examine the associated heterophoria of a subject with the cross test described, for example, on page 248 in the Handbuch für Augenoptik (Handbook of Ophthalmic Optics), published by Carl Zeiss, 4th edition 2000. In the cross test, the subject captures the portion 54 of the pattern with one eye, for example, the left one, and captures the portion 56, separately therefrom, with the other.

FIG. 7b shows a test pattern 58. The test, pattern 58 can be used to examine the associated heterophoria of a subject with the rectangle test, which is likewise described, for example, on page 248 in the Handbuch für Augenoptik (Handbook of Ophthalmic Optics), published by Carl Zeiss, 4th edition 2000. In the rectangle test, the subject captures the portion 60 of the patterns with one eye, the portion 62 with the other one, and the portion 64 with both eyes. In order to visualize the test pattern 58 with the eyesight testing device 2, for example, the portion 60 and the portion 64 are displayed on the display unit 14 in the display-unit zones 30a, 30b. 30c, . . . The portion 62 and the portion 64 are displayed in the display-unit zones 34a, 34b, 34c, . . .

FIG. 7c shows a further test pattern 66. The test pattern 66 can be used to examine the associated heterophoria of a subject with the triangle test, which is likewise described, for example, on page 248 in the Handbuch für Augenoptik (Handbook of Ophthalmic Optics), published by Carl Zeiss, 4th edition 2000, In the triangle test, the subject, captures the portions (68, 69) of the pattern with one eye, the portions (70, 71) with the other one, and the portions (72, 74, 76) with both eyes. In order to visualize the test pattern 56 with the eyesight testing device 2, for example, the portions 68 and 72, 74, 76 are displayed on the display unit 14 in the display-unit zones 30a, 30b, 30c, . . . and the portions 70, 72, 74, 76 are displayed in the display-unit zones 34a, 34b, 34c, . . .

The test pattern 78 shown in FIG. 7d serves for examining the associated heterophoria of a subject with the stereo balance test, which is also described, for example, on page 248 in the Handbuch für Augenoptik (Handbook of Ophthalmic Optics), published by Carl Zeiss, 4th edition 2000. In the stereo balance test, the subject captures the portions (80, 81) of the pattern with one eye, the portions (82, 83) with the other one, and the portions 84, 86 and 88 with both eyes. In order to visualize the test pattern 78 with the eyesight testing device 2, for example, the portions 80, 81 and 84, 86, 88 are displayed on the display unit 14 in the display-unit zones 30a, 30b, 30c, . . . and the portions 82, 83 and 84, 86, 88 are displayed in the display-unit zones 34a, 34b, 34c, . . .

It should be noted that, unlike the case in the illustration of FIGS. 6a to 6d, the various portions of the test patterns 52, 58, 66 and 78 shown there can be perceived by a subject, depending on the type of visual defect, to be horizontally and/or vertically offset, twisted with respect to one another or of different size.

Figure 8:
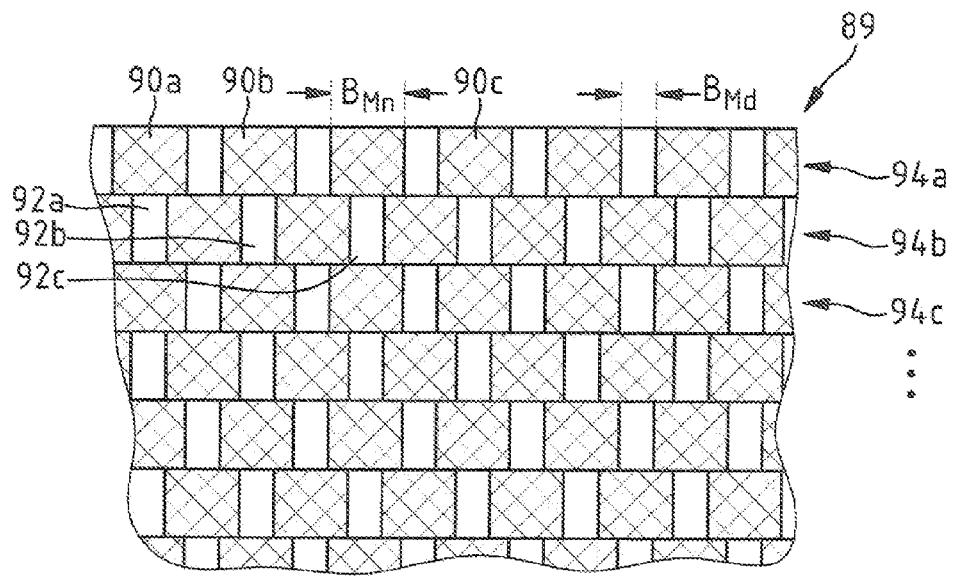
FIG. 8 shows one alternative configuration of a mask in a screen system of the eyesight testing device.

FIG. 8 shows a portion of an alternative embodiment of a mask 89 for the screen system 36. The mask 89 has regions 90a, 90b, 90c, . . . , which are arranged offset with respect to one another and are opaque for the light from the display unit 14.

The regions 92a, 92b, 92c, . . . of the mask 89 are complementary to the regions 90a, 90b, 90c, . . . The regions 92a, 92b , 92c, . . . are transmissive for the light from the display unit 14.

The regions 90a, 90b, 90c, . . . and the regions 92a, 92b, 92c, . . . , 94b, 94c, . . . are in each case rectangular. The regions 90a, 90b, 90c, . . . and 92a, 92b, 92c are arranged in successive rows 94. In mutually adjacent rows 94a, 94b; 94b, 94c, the regions 92a, 92b, 92c, . . . which are transmissive for light are positioned to be offset with respect to the regions 90a, 90b, 90c, . . . which are opaque for light. The width $B_{Mu}$ of the regions 92a, ,92b, 92c, . . . which are opaque for light is greater than the width $B_{Md}$ of the regions, which are transmissive for light. Preferably in this case:

$$B_{Md} = \frac{1}{2} B_{Mu}.$$

Figure 9:
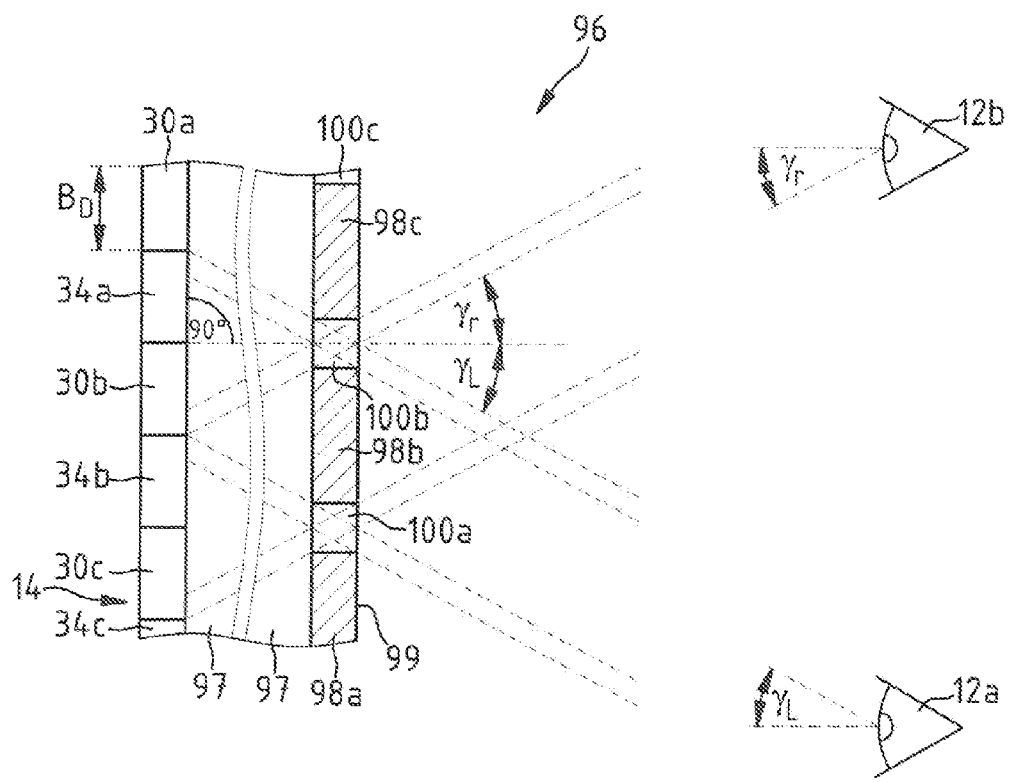
FIG. 9 shows a further alternative configuration of a mask in a screen system of the eyesight testing device.

FIG. 9 shows a mask 96 as an alternative embodiment of a mask 37 for the screen system 36. The mask 96 is configured as an LCD screen 99. The LCD screen has gap-shaped regions 98a, 98b, 98c, . . . , 100a, 100b, 100c, . . . , which can be switched to be optionally transmissive or opaque for the light from the display unit 14 using a control device (not shown). The geometry, that is, in particular the width $B_D$ of the display-unit zones 30a, 30b, 30c, . . . ; 34a, 34b, 34c, . . . and the width ($B_{Mn}$, $B_{Md}$) of the regions 98a, 98b, 98c, . . . , 100a, 100b, 100c, of the mask 96 can be adjusted here using the computer 20 in the eyesight testing device 2. In order to match, the eyesight testing device 2 to the position of the eyes of an observer, the positions and dimensions of the regions 98a, 98b, 98c, . . . , which are transmissive for light and the sectors 100a, 100b, 100c, . . . which are opaque for light are adjusted here, on the basis of the angular position of the eyes (12a, 12b) of the subject 6, using the computer 20 shown in FIG. 1 such that the subject 6 sees with his left and right eyes (12a, 12b) partial patterns, produced using the display unit 14, which are separated from one another exactly.

The mask 96 with the LCD screen 99 is connected to the display unit 14 via a transparent glass body 97. The mask 96 is arranged such that it cannot move with respect to the display unit 14. In principle, however, moveability with respect to the display unit 14 can also be provided if the mask 96 is used in a corresponding eyesight testing device 2.

Figure 10:
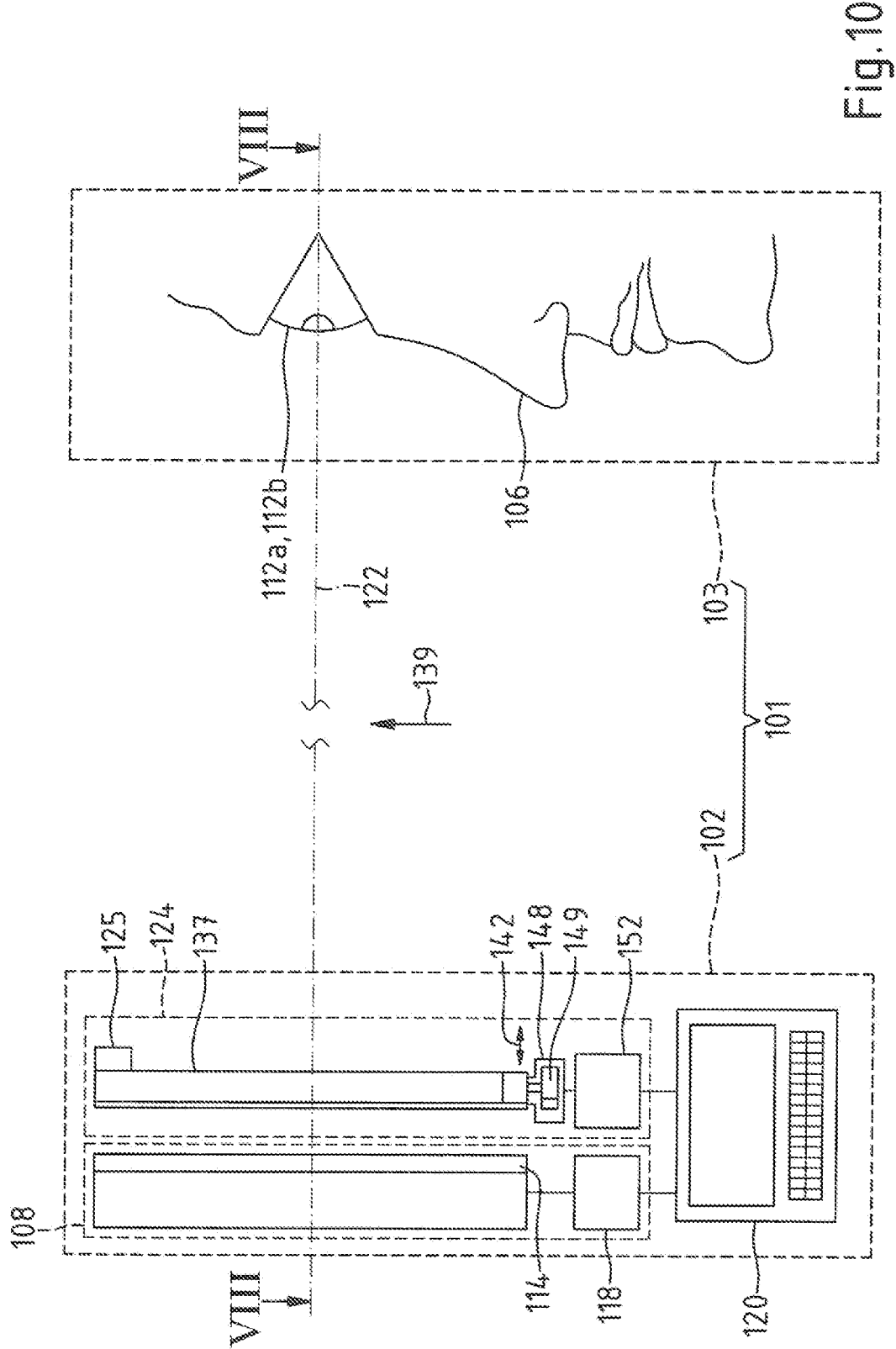
FIG. 10 shows a further examination device with an eyesight testing device, which contains a display unit having a prism matrix; and, FIG. 11 shows a section through the eyesight testing device having the prism matrix along the line VIII-VIII in FIG. 10.

FIG. 10 shows a further examination device 101 having an eyesight testing device 102. The eyesight testing device 102 is also configured to display unit test patterns, which are generated using an image generation apparatus 108, to the eyes (112a, 112b) of a subject 106. To the extent that the elements in FIG. 10 functionally correspond to the elements in FIG. 1, they are followed in FIG. 10 with reference signs that are increased by the number 100. Unlike in the eyesight testing device 2 from FIG. 1, the optical assembly 124 in the eyesight testing device 102 contains a prism matrix 137 instead of the screen system.

The prism matrix 137 can be displaceable with respect to the display unit 114. Such displaceability, however, is not absolutely necessary. If the prism matrix 137 is displaceable, it is expedient if the latter can be moved, in accordance with the double-headed arrow 147, in particular in a direction, that is perpendicular with respect to the plane of the display unit 114, and/or in one or more directions which are perpendicular to the double-headed arrow 147.

Figure 11:
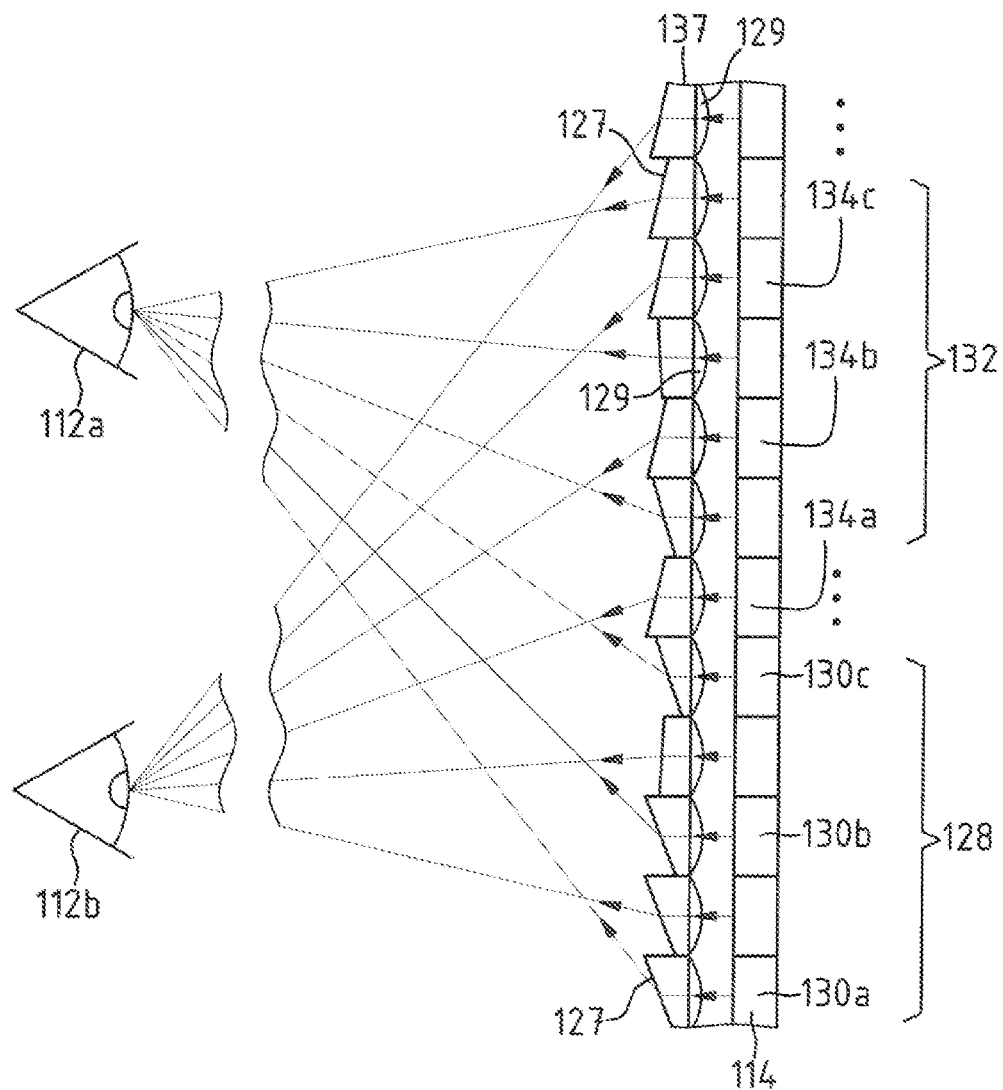

FIG. 11 is a partial section through the eyesight testing device 102 along the line VIII-VIII in FIG. 10. The prism matrix 137 has a multiplicity of different prism portions 127, which extend in the vertical direction 139. The prism portions 127 have a region 129 which faces the display unit 114 and is shaped, like a convex cylindrical lens which extends in the vertical direction of the prism portion 127 and has a cylinder axis parallel to the vertical direction 139. Alternatively, it is also possible to provide successive converging lenses instead of a cylindrical lens. The prism portions 127 are used to direct the light of the pixels of the display unit 114 in the first group 128 of the image points produced in the zones 130a, 130b, 130c, on the basis of refraction, with a directed beam path to the left eye 112a of a subject, who is located in the subject region 103 of the examination system 101. Accordingly, the light of the second group 132 of the image points produced in the zones 134a, 124b, 134c, . . . is directed, on the basis of refraction, with a directed beam path to the right eye 112b of the subject 106. By way of the cylindrically shaped regions 129 of the prism portions or by means of an arrangement of a lens array at this location, it is possible, similarly to the case of the eyesight testing device 2 described with reference to FIG. 1 to FIG. 9, for partial patterns, which are separated exactly for the left and right eyes, to be displayed for a subject 106 in a specific distance region from the eyesight testing device and for various head positions that lie within a certain tolerance range.

On the basis of the directed beam path, the use of the prism matrix 137 in the eyesight testing device 102 offers the advantage that from the visual impression of a pattern, which is visualized to a subject during an eyesight test, it is possible to conclude with a high degree of reliability that a visual defect is present or absent: this is because artefacts caused by an unfavorable head position in the subject's visual impression are largely ruled out here.

In conclusion, the following preferred features of the invention should be emphasized: the invention relates to an eyesight testing device (2, 102) for examining associated heterophoria of the eyes (12a, 12b, 112a, 112b) of a subject (6, 106). The eyesight testing device (2, 102) contains an image generation apparatus (8, 108), which has a display unit (14, 114) for producing test patterns, which can be displayed to the eyes (12a, 12b, 112a, 112b) of the subject (6, 106) with an optical beam path (22, 122). In the eyesight testing device, on that side 26 of the display unit (14, 114) which in the optical beam path (22, 122) faces the eyes (12a, 12b, 112a, 112b) of the subject, an optical assembly (24, 124) is arranged. The optical assembly (24, 124) separates the light supplied by a first group (28, 128) of selected zones (30a, 30b, 30c, 30d; 130a, 130b, 130c) of the display unit 14 to the optical beam path 22 from the light that is supplied to the beam path 22 by a second group (32, 132) of selected zones (34a, 34b, 34c, 34d; 134a, 134b, 134c) of the display unit 14. The left eye (12a, 112a) of the subject (6, 106) thus only receives the light from the first group (28, 128) of selected zones (30a, 30b, 30c, 30d; 130a, 130b, 130c) of the display unit (14, 114). The light from the second group (32, 132) of selected zones (34a, 34b, 34c, 34d; 134a, 134b, 134c) of the display unit (14, 114) then only arrives at the right eye (12b, 112b) of the subject (6, 106). The optical assembly 124 comprises a prism matrix 137, which has a multiplicity of prism portions which extend in the vertical direction 139 and in each case have a lens-shaped, in particular cylindrical-lens-shaped, region with a convex surface facing the display unit 114. The optical assembly 24 can alternatively also contain a specific screen system 36 acting as a parallax barrier, with which screen system the light of the first and second groups (28, 32; 128, 132) of selected zones (30a, 30b, 30c, 30d; 34a, 34b, 34c, 34d) of the display unit (14, 114) is separated.

It is understood that the foregoing description is that of the preferred embodiments of the invention and that various changes and modifications may be made thereto without departing from the spirit and scope of the invention as defined in the appended claims.

What is claimed is:

1. A vision testing apparatus for examining heterophoria of the eyes of a subject, the vision testing apparatus comprising:
an image generating device including a display for generating test patterns which can be displayed via an optical beam path to the eyes of said subject;
said display having a side facing toward the eyes of the subject in said optical beam path;
said display having a first group of selected zones supplying a first light to said optical beam path and a second group of selected zones supplying a second light to said optical beam path;
an optical component assembly arranged on said side of said display and including a prism matrix configured to separate said first light from said second light to supply the left eye with said first light from said first group and to supply the right eye with said second light from said second group;
said prism matrix having a plurality of prism sections extending in a vertical direction; and,
said prism sections having respective lens-shaped regions facing toward said display and each of said lens-shaped regions having a convex surface.

2. The vision testing apparatus of claim 1, wherein each of said lens-shaped regions is a cylinder-lens-shaped region.

3. The vision testing apparatus of claim 1, wherein said display has a plurality of pixels for generating image points in mutually complementary ones of said zones; said pixels extend in a vertical direction; and, said lens-shaped regions of said prism sections are cylinder-lens-shaped and define respective cylinder axes extending in said vertical direction.

4. The vision testing apparatus of claim 1, wherein said optical component assembly is adjustable for fixing the course of the optical beam path to the eyes of the subject.

5. A vision testing apparatus for examining heterophoria of the eyes of a subject, the vision testing apparatus comprising:
an image generating device including a display for generating test patterns which can be displayed via an optical beam path to the eyes of said subject;
said display having a side facing toward the eyes of the subject in said optical beam path;
said display having a first group of selected zones supplying a first light to said optical beam path and a second group of selected zones supplying a second light to said optical beam path;
an optical component assembly arranged on said side of said display and including a diaphragm system to separate said first light from said second light to supply the left eye with said first light from said first group and to supply the right eye with said second light from said second group;
said diaphragm system functioning as a parallax barrier and said diaphragm system including a mask having alternating opaque and light transmissive regions;
said display having a plurality of pixels for generating image points in mutually complementary ones of said zones and said pixels extending in a vertical direction;
said mutually complementary zones of said display being configured to be strip shaped and the width ($B_{Mn}$) of said opaque regions of said mask and the width ($B_{Md}$) of said light transmissive regions of said mask as well as the width ($B_D$) of said strip-shaped zones of said display satisfy the relationship:

$$B_{Mn} \approx 3B_{Md} \approx \frac{3}{2}B_D$$

wherein a distance (z) of said mask from said display corresponds to 25 to 50 times the width ($B_D$) of said zones of said display.

6. The vision testing apparatus of claim 5, wherein said optical component assembly is adjustable for fixing a course of said optical beam path to the eyes of said subject.

7. The vision testing apparatus of claim 6, wherein said width ($B_D$) of said strip-shaped zones of said display and said widths ($B_{Md}$, $B_{Mn}$) of said light transmissive regions for the light of said display and said opaque regions of said mask are adjustable.

8. The vision testing apparatus of claim 7, wherein said display has a plurality of pixels for generating image points; and, said width ($B_D$) of said strip-shaped zones of said display corresponds to a diameter (P) of one of said pixels of said display.

9. The vision testing apparatus of claim 8, wherein said diaphragm system defines a light transmissive plane separating the light for the left and right eyes and said diaphragm system is movable perpendicularly and/or parallel relative to said display; and, wherein at least said distance (z) can be varied between said light transmissive plane and at least one of the following: said display; a position of the alternating light transmissive regions and opaque regions in a light pass-through plane of said diaphragm system.

10. The vision testing apparatus of claim 9, further comprising:
a detecting device for detecting the angular position of the eyes of the subject;
the eyes of said subject defining a pupil distance (PD);
a drive coupled to said detecting device and said drive being configured to displace said diaphragm system in response to a detected angular position of the eyes of said subject so as to cause an offset (S) of a center of a perpendicular projection of said pupil distance (PD) from a vertical line at the center of said mask in advance of the displacement and a vertical displacement (V) of the center of said mask after said displacement to satisfy the relationship:

$$\frac{V}{z} = \frac{S}{g_0},$$

wherein said distance (z) is the distance of the light transmissive plane of said diaphragm system from said display and ($g_0$) is the distance of said subject from said light transmissive plane of said diaphragm system.

11. The vision testing apparatus of claim 5, wherein said display has a plurality of pixels for generating image points in mutually complementary ones of said zones; and, said pixels extend in a vertical direction.

12. The vision testing apparatus of claim 11, wherein said width ($B_{Mn}$) is a horizontal width of said opaque region of said mask; and, said horizontal width ($B_{Mn}$) is at least twice as large as said width ($B_{Md}$) of said light tranmissive regions of said mask.

13. The vision testing apparatus of claim 5, wherein said width ($B_D$) of said strip-shaped zones of said display corresponds to a diameter (P) of a display pixel for generating an image point.

14. An examining arrangement for examining heterophoria of the eyes of a subject, said examining arrangement comprising:
a vision testing apparatus for examining heterophoria of the eyes of a subject, the vision testing apparatus including:
an image generating device including a display for generating test patterns which can be displayed via an optical beam path to the eyes of said subject;
said display having a side facing toward the eyes of the subject in said optical beam path;
said display having a first group of selected zones supplying a first light to said optical beam path and a second group of selected zones supplying a second light to said optical beam path;
an optical component assembly arranged on said side of said display and being configured to separate said first light from said second light to supply the left eye with said first light from said first group and to supply the right eye with said second light from said second group;
said optical component assembly including a prism matrix having a plurality of prism sections extending in a vertical direction;
said prism sections having respective lens-shaped regions facing toward said display and each of said lens-shaped regions having a convex surface;
a region for the subject wherein said subject can be positioned, for carrying out a vision test, at a distance (A) from said display of said vision testing apparatus; and,
said distance (A) lying in a range of 1 meter≤A≤7 meters.

15. The examining arrangement of claim 14, wherein said distance (A) lies in a range of 2 meters≤A≤3 meters.

16. An examining arrangement for examining heterophoria of the eyes of a subject, said examining arrangement comprising:
a vision testing apparatus for examining heterophoria of the eyes of a subject, the vision testing apparatus including:
an image generating device including a display for generating test patterns which can be displayed via an optical beam path to the eyes of said subject;
said display having a side facing toward the eyes of the subject in said optical beam path;
said display having a first group of selected zones supplying a first light to said optical beam path and a second group of selected zones supplying a second light to said optical beam path;
an optical component assembly arranged on said side of said display and including a diaphragm system to separate said first light from said second light to supply the left eye with said first light from said first group and to supply the right eye with said second light from said second group;
said diaphragm system functioning as a parallax barrier and said diaphragm system including a mask having alternating opaque and light transmissive regions;
said display having a plurality of pixels for generating image points in mutually complementary ones of said zones and said pixels extending in a vertical direction;
said mutually complementary zones of said display being configured to be strip shaped and the width ($B_{Mn}$) of said opaque regions of said mask and the width ($B_{Md}$) of said light transmissive regions of said mask as well as the width ($B_D$) of said strip-shaped zones of said display satisfy the relationship:

$$B_{Mn} \approx 3B_{Md} \approx \frac{3}{2}B_D$$

wherein a distance (z) of said mask from said display corresponds to 25 to 50 times the width ($B_D$) of said zones of said display;
a region for the subject wherein said subject can be positioned, for carrying out a vision test, at a distance (A) from said display of said vision testing apparatus; and,
said distance (A) lying in a range of 1 meter≤A≤7 meters.

17. The examining arrangement of claim 16, wherein said distance (A) lies in a range of 2 meters≤A≤3 meters.

18. A method for examining heterophoria of the eyes of a subject with a vision testing apparatus including: an image generating device including a display for generating test patterns which can be displayed via an optical beam path to the eyes of said subject; said display having a side facing toward the eyes of the subject in said optical beam path; said display having a first group of selected zones supplying a first light to said optical beam path and a second group of selected zones supplying a second light to said optical beam path; an optical component assembly arranged on said side of said display and being configured to separate said first light from said second light to supply the left eye with said first light from said first group and to supply the right eye with said second light from said second group; said optical component assembly including a prism matrix having a plurality of prism sections extending in a vertical direction; and, said prism sections having respective lens-shaped regions facing toward said display and each of said lens-shaped regions having a convex surface; and the method comprising the steps of:
generating two component patterns, which are at least section-wise mutually complementary, utilizing said first and second groups of selected zones of said display;
bringing one of said component patterns to display for the left eye of said subject; and,
bringing the other one of said component patterns to display for the right eye of said subject.

19. The method of claim 18, wherein said component patterns are for carrying out the cross test or the rectangular test or the triangle test or the stereo vision balance test.

20. A method for examining heterophoria of the eyes of a subject with a vision testing apparatus including: an image generating device including a display for generating test patterns which can be displayed via an optical beam path to the eyes of said subject; said display having a side facing toward the eyes of the subject in said optical beam path; said display having a first group of selected zones supplying a first light to said optical beam path and a second group of selected zones supplying a second light to said optical beam path; an optical component assembly arranged on said side of said display and including a diaphragm system to separate said first light from said second light to supply the left eye with said first light from said first group and to supply the right eye with said second light from said second group; said diaphragm system functioning as a parallax barrier and said diaphragm system including a mask having alternating opaque and light transmissive regions; said display having a plurality of pixels for generating image points in mutually complementary ones of said zones and said pixels extending in a vertical direction; said mutually complementary zones of said display being configured to be strip shaped and the width ($B_{Mn}$) of said opaque regions of said mask and the width ($B_{Md}$) of said light transmissive regions of said mask as well as the width ($B_D$) of said strip-shaped zones of said display satisfy the relationship:

$$B_{Mn} \approx 3 B_{Md} \approx \frac{3}{2} B_D$$

wherein a distance (z) of said mask from said display corresponds to 25 to 50 times the width ($B_D$) of said zones of said display; and, the method comprising the steps of:
  generating two component patterns, which are at least section-wise mutually complementary, utilizing said first and second groups of selected zones of said display;
  bringing one of said component patterns to display for the left eye of said subject; and,
  bringing the other one of said component patterns to display for the right eye of said subject.

21. The method of claim 20, wherein said component patterns are for carrying out the cross test or the rectangular test or the triangle test or the stereo vision balance test.

\* \* \* \* \*

UNITED STATES PATENT AND TRADEMARK OFFICE
CERTIFICATE OF CORRECTION

PATENT NO. : 8,827,451 B2  
APPLICATION NO. : 13/724961  
DATED : September 9, 2014  
INVENTOR(S) : Jesus-Miguel Cabeza Guillen et al.

Page 1 of 2

It is certified that error appears in the above-identified patent and that said Letters Patent is hereby corrected as shown below:

In the Specification,

In Column 1:  
Line 7: delete "201.1" and substitute -- 2011 -- therefor.

In Column 2:  
Line 8: delete "front" and substitute -- from -- therefor.

In Column 3:  
Line 13: delete "far" and substitute -- for -- therefor.  
Line 28: delete "$B_{Mu} \sim 3B_{Md} \sim 3/2B_D$." and substitute -- $B_{Mu} \approx 3B_{Md} \approx 3/2B_D$, -- therefor.  
Line 58: delete "foe" and substitute -- be -- therefor.  
Line 60: delete "snows" and substitute -- shows -- therefor.

In Column 4:  
Line 33: delete "A~2.5 m" and substitute -- A≈2.5 m -- therefor.

In Column 5:  
Line 32: delete "least;" and substitute -- least -- therefor.  
Line 59: delete "$B_{Md}=1/28_D$." and substitute -- $B_{Md}=1/2B_D$. -- therefor.

In Column 6:  
Line 13: delete "35" and substitute -- 36 -- therefor.

In Column 7:  
Line 9: delete "30c, . . . ," and substitute -- 30c , . . . ; -- therefor.  
Line 43: delete "Δ," and substitute -- Δ`, -- therefor.

Signed and Sealed this  
Twenty-seventh Day of January, 2015

Michelle K. Lee  
*Deputy Director of the United States Patent and Trademark Office*

Line 50: delete "$\Delta = \left(1 - \frac{B_{Md}}{B_{Mu}}\right)\Delta.$" and substitute -- $\Delta` = \left(1 - \frac{B_{Md}}{B_{Mu}}\right)\Delta.$ -- therefor.
Line 60: delete "β≤1." and substitute -- β≤1`. -- therefor.
Line 61: delete "si" and substitute -- a -- therefor.

In Column 8:
Line 3: delete "distances" and substitute -- distance -- therefor.
Line 25: delete "test," and substitute -- test -- therefor.
Line 44: delete "2000," and substitute -- 2000. -- therefor.
Line 44: delete "subject," and substitute -- subject -- therefor.
Line 47: delete "56" and substitute -- 66 -- therefor.

In Column 10:
Line 23: delete "124b," and substitute -- 134b, -- therefor.